(12) United States Patent
Toth et al.

(10) Patent No.: US 6,968,042 B2
(45) Date of Patent: Nov. 22, 2005

(54) METHODS AND APPARATUS FOR TARGET ANGLE HEEL EFFECT COMPENSATION

(75) Inventors: Thomas Louis Toth, Brookfield, WI (US); Bruce Matthew Dunham, Mequon, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 131 days.

(21) Appl. No.: 10/661,844

(22) Filed: Sep. 12, 2003

(65) Prior Publication Data
US 2005/0058254 A1 Mar. 17, 2005

(51) Int. Cl.⁷ .............................................. G21K 3/00
(52) U.S. Cl. ...................... 378/156; 378/158; 378/119
(58) Field of Search ................................ 378/147, 156, 378/157, 158, 159, 160, 4, 148, 153, 161, 378/119, 140, 143, 121

(56) References Cited

U.S. PATENT DOCUMENTS

| | | | |
|---|---|---|---|
| 2,225,940 A * | 12/1940 | Grossmann | 378/98 |
| 4,048,507 A | 9/1977 | de Gaston | |
| 4,101,766 A * | 7/1978 | Minami et al. | 378/158 |
| 4,107,562 A * | 8/1978 | Koller et al. | 378/203 |
| 4,126,789 A | 11/1978 | Vogl et al. | |
| 4,181,858 A * | 1/1980 | Moore | 378/18 |
| 4,321,471 A | 3/1982 | Holland et al. | |
| 4,336,476 A | 6/1982 | Holland et al. | |
| 4,355,409 A | 10/1982 | Amplatz | |
| 4,361,899 A | 11/1982 | Amplatz | |
| 4,499,591 A * | 2/1985 | Hartwell | 378/62 |
| 4,763,343 A | 8/1988 | Yanaki | |
| RE33,634 E | 7/1991 | Yanaki | |
| 5,745,546 A | 4/1998 | Hell et al. | |
| 6,215,846 B1 | 4/2001 | Mazess et al. | |
| 6,282,261 B1 | 8/2001 | Mazess et al. | |
| 6,315,445 B1 | 11/2001 | Mazess et al. | |
| 6,320,931 B1 | 11/2001 | Arnold | |
| 6,418,193 B1 * | 7/2002 | Albagli | 378/158 |
| 6,522,721 B1 | 2/2003 | Lustberg | |

\* cited by examiner

*Primary Examiner*—Edward J. Glick
*Assistant Examiner*—Irakli Kiknadze
(74) *Attorney, Agent, or Firm*—Carl B. Horton, Esq.; Armstrong Teasdale LLP (57) ABSTRACT

A method of at least partially compensating for an x-ray tube target angle heel effect includes positioning a filter having an anode side and a cathode side between an x-ray source and an x-ray detector, wherein the cathode side has a higher attenuation coefficient than the anode side, to at least partially compensate for the target angle heel effect.

37 Claims, 5 Drawing Sheets

Anode side    Cathode side

METHODS AND APPARATUS FOR TARGET ANGLE HEEL EFFECT COMPENSATION

BACKGROUND OF THE INVENTION

This invention relates generally to Computed Tomography (CT) imaging systems, and more particularly, to target angle heel effect compensation.

In at least some known imaging systems, an x-ray tube source projects an x-ray beam which passes through an object being imaged, such as a patient, and impinges upon an array of x-ray detector rows. The heel effect from an x-ray tube is well known. An x-ray tube source includes an anode side and a cathode side. The anode side is also known as the target, which is bombarded with electrons to generate x-ray beam radiation. X-rays from the x-ray tube are generated at a small depth inside the target (anode) of the x-ray tube. X-rays traveling toward an anode side of an object being scanned travel through more volume of the target than x-rays traveling toward a cathode side of the object. Therefore, x-rays traveling toward the anode side leave the target more attenuated than x-rays traveling toward the cathode side. This attenuation difference is called the heel effect.

With the advent of multislice CT imaging systems including a plurality of detector rows, the heel effect can produce image quality differences over the detector rows. For example, a 40 mm Volumetric Computed Tomography (VCT) detector with a nominal 7 degree target angle has an effective target angle of 5 degrees on the outer anode side row and 9 degrees on the outer cathode side row, resulting in a 20% effective signal difference between the anode side and the cathode side. This variance in radiation intensity due to the heel effect reduces image quality over the x-ray detector rows, and therefore reduces the image quality of the radiographs.

BRIEF DESCRIPTION OF THE INVENTION

In one aspect, a method of at least partially compensating for an x-ray tube target angle heel effect is provided. The method includes positioning a filter having an anode side and a cathode side between an x-ray source and an x-ray detector, wherein the cathode side has a higher attenuation coefficient than the anode side, to at least partially compensate for the target angle heel effect.

In another aspect, an x-ray tube is provided. The x-ray tube includes an anode, a cathode, a beryllium window, and a material deposited on the window, wherein the material is wedge shaped, wherein the wedge shape includes a horizontal top, a bottom, a first vertical side and a second vertical side, wherein the horizontal top and the bottom are not parallel and wherein the first vertical side and the second vertical side are unequal in length.

In another aspect, an imaging system for scanning an object is provided. The system includes a radiation source, a radiation detector positioned to receive radiation from the radiation source, a computer operationally coupled to the radiation source and the radiation detector, and a filter having an anode side and a cathode side, positioned between the source and the detector, wherein the cathode side has a higher attenuation coefficient than the anode side, to at least partially compensate for a target angle heel effect.

In yet another aspect, a Computed Tomography (CT) imaging system for scanning an object is provided. The system includes an x-ray source, an x-ray detector positioned to receive x-rays from the source, a computer operationally coupled to the x-ray source and the x-ray detector, and a filter having an anode side and a cathode side, positioned between the source and the detector, wherein the cathode side has a higher attenuation coefficient than the anode side, to at least partially compensate for a target angle heel effect.

DETAILED DESCRIPTION OF THE INVENTION

In some known CT imaging system configurations, an x-ray source projects a fan-shaped beam which is collimated to lie within an X–Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
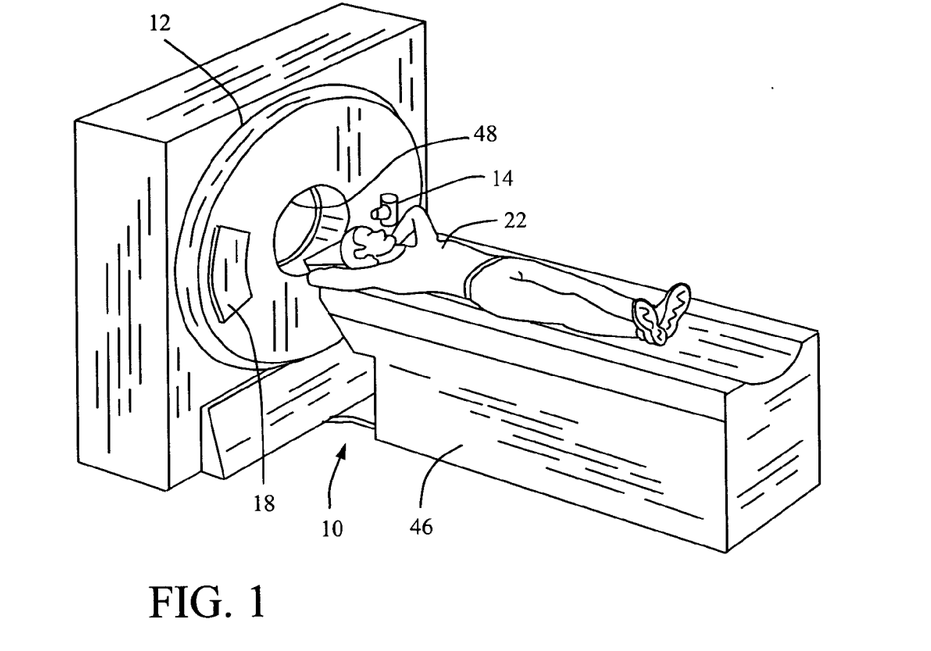
FIG. 1 is a pictorial view of a CT imaging system.
Figure 2:
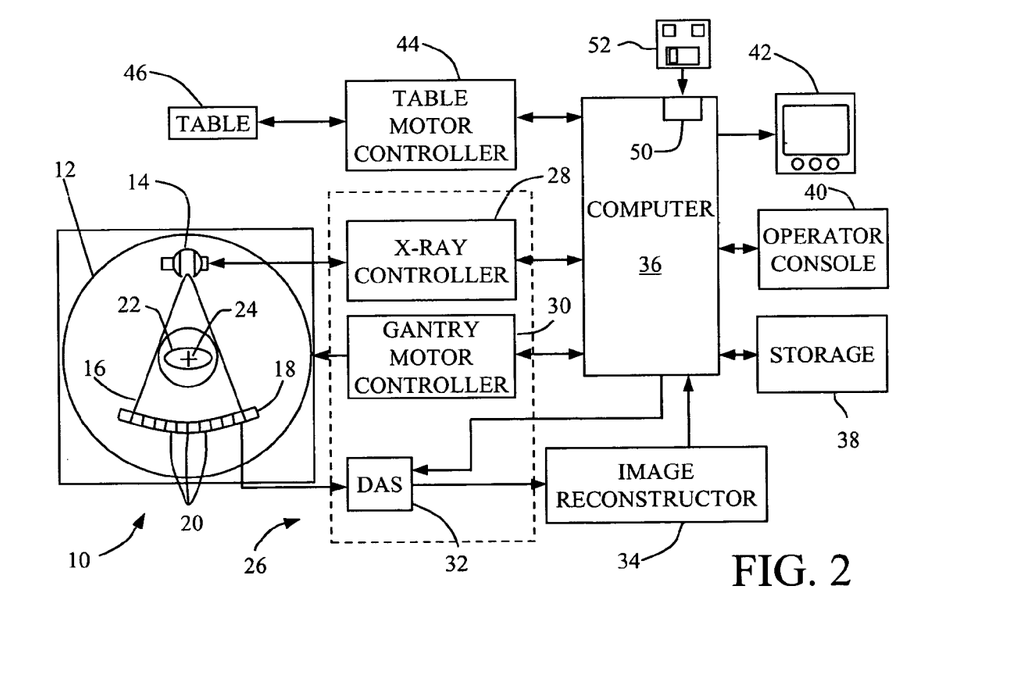
FIG. 2 is a block schematic diagram of the system illustrated in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source). Additionally, it is contemplated that the benefits of the invention accrue to imaging modalities other than CT. Additionally, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Herein described are methods and apparatus to at least partially compensate for the heel effect by balancing the radiation intensity of the x-ray beam emitted to the x-ray detector rows, in one embodiment, using a wedge shaped compensation filter.

A used herein, the term "wedge shaped" is defined as a shape including a horizontal top, a bottom, a first vertical side and a second vertical side, wherein the horizontal top and the bottom are not parallel and wherein the first vertical side and the second vertical side are unequal in length.

Figure 3:
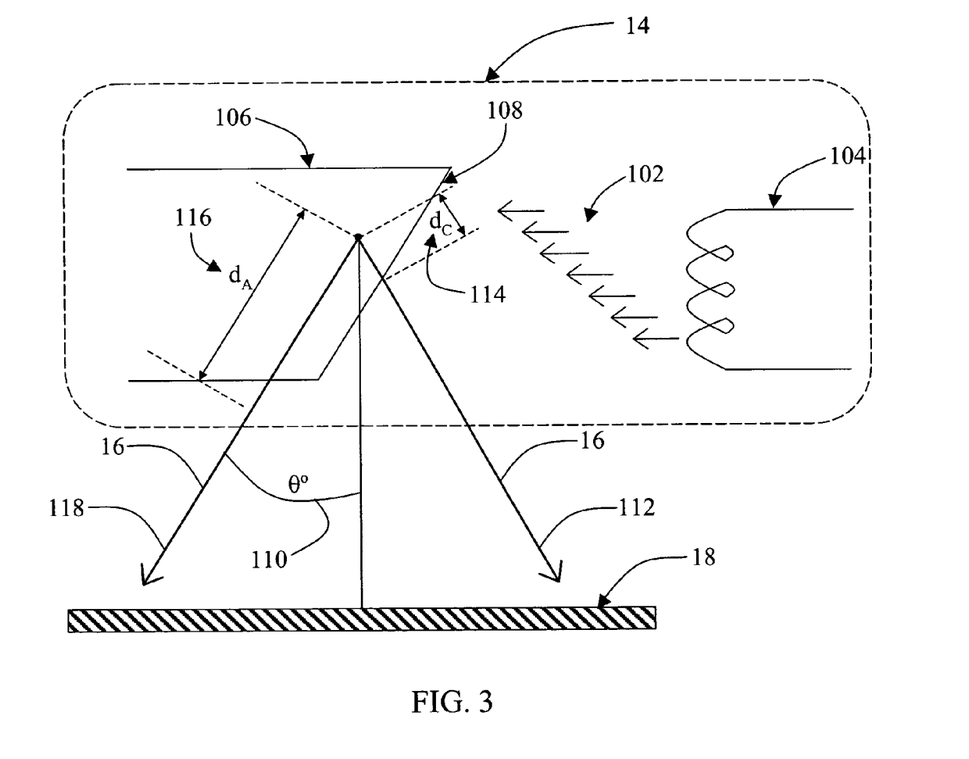
FIG. 3 illustrates the target angle and the heel effect.

FIG. 3 illustrates target angle heel effect x-ray beams 16. Electrons 102 travel inside x-ray tube 14 from a cathode side 104 to an anode side 106 and collide with a target 108. Electrons 102 make contact with target 108 at different locations along target 108, and cause the emission of x-rays 16 at different angles on leaving target 108. The angle between target 108 and the perpendicular to x-ray detector rows 18 is a target angle 110. An x-ray 112 emitted from target 108 travels a distance $d_c$ 114 within target 108 before exiting target 108 toward cathode side 104. This is a shorter distance than a distance $d_A$ 116 that an x-ray 118 travels within target 108 before exiting target 108 toward anode side 106. Since $d_A$ 116 is greater than dc 114, then x-ray 118 leaves target 108 more attenuated than x-ray 112. This difference in attenuation is the heel effect.

Figure 4:
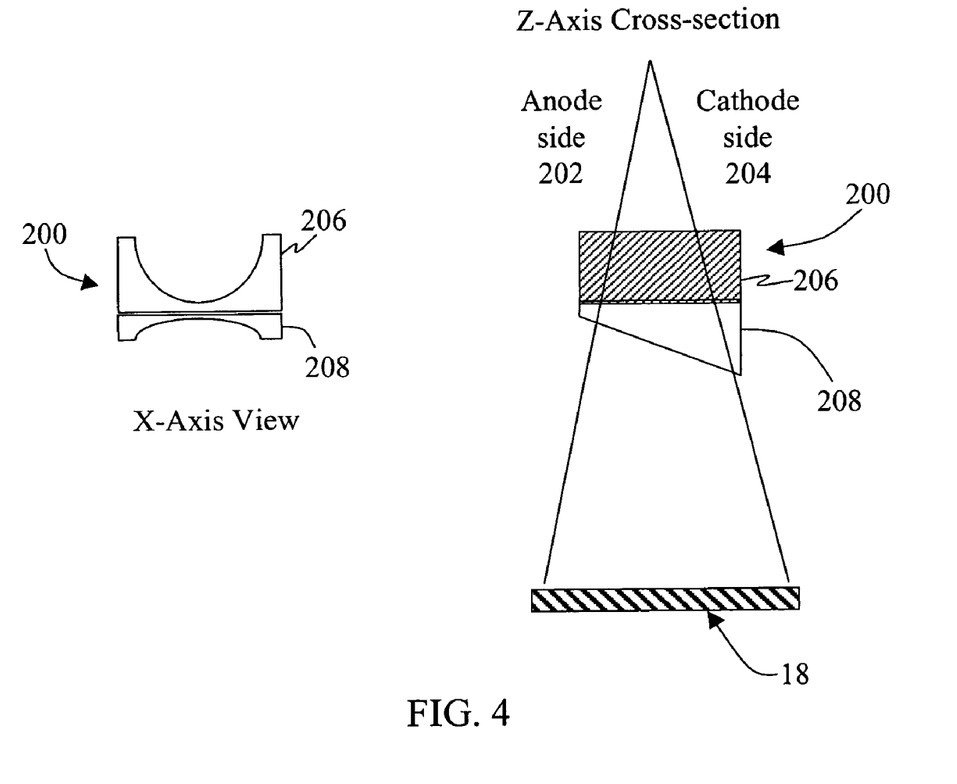
FIG. 4 shows a wedge shaped filter in relation to a known filter.

FIG. 4 illustrates a heel effect compensation filter 200 with an x-axis view and a z-axis cross-sectional view at isocenter. Filter 200 includes an anode side 202 and a cathode side 204. Filter 200 includes a graphite portion 206 and an aluminum portion 208. In one embodiment, aluminum portion 208 is entirely made of aluminum. In an alternative embodiment, aluminum portion 208 is an aluminum alloy. As seen in the z-axis cross-sectional view, aluminum portion 208 is thicker on cathode side 204 than on anode side 202. In an exemplary embodiment cathode side 204 of portion 208 is about 1 mm thicker than anode side 202 of portion 208. In other embodiments the thickness difference is between about 0.5 mm and about 1.5 mm.

Because cathode side 204 of portion 208 is thicker than anode side 202, x-rays passing through cathode side 204 are more attenuated by portion 208 than x-rays passing through anode side 202 which compensates at least partially for the heel effect.

As illustrated in U.S. Pat. No. 6,263,046 to Rogers, which is hereby incorporated in its entirety, an x-ray tube is mounted within a casing wherein the x-ray tube and the casing both have an x-ray transmissive window constructed from an x-ray transmissive material such as beryllium, aluminum or titanium.

Figure 5:
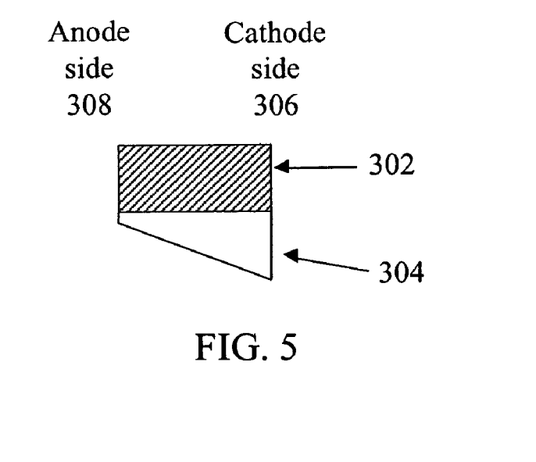
FIG. 5 shows a wedge shaped filter in relation to an x-ray tube window.

FIG. 5 illustrates an x-ray tube window 302 that x-ray beam 16 (shown in FIG. 3) emitted from target 108 (shown in FIG. 3) passes through on exiting x-ray tube 14 (shown in FIG. 3). A wedge shaped filter 304 is shown deposited directly onto window 302, such as a beryllium window, of x-ray tube 14. Various materials can be used for wedge shaped filter 304, including but not limited to, aluminum or copper. Wedge filter 304 is thicker on a cathode side 306 than on an anode side 308. The thickness of wedge shaped filter 304 used is determined by the attenuation properties of the material used. The difference in thicknesses of cathode side 306 and anode side 308 is selected based on both the material used to fabricate filter 304 and the heel effect of target 108.

Figure 6:
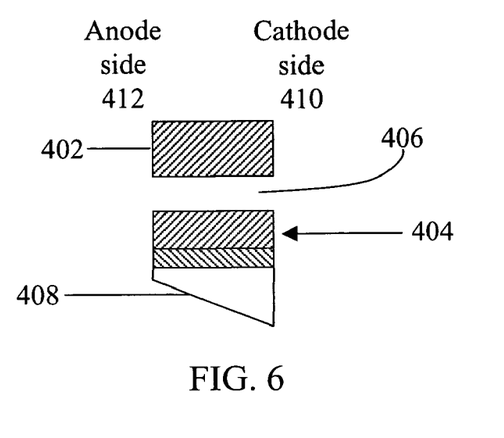
FIG. 6 shows a wedge shaped filter in relation to an x-ray tube casing filter.

FIG. 6 illustrates an x-ray tube window 402 and an x-ray tube casing window 404 separated from x-ray tube window 402 by an oil gap 406. In one embodiment, at least some partial heel effect compensation is accomplished by depositing a wedge shaped filter 408 directly on casing window 404. Wedge filter 408 is thicker on a cathode side 410 than on an anode side 412. Casing window 404 is sometimes fabricated to have a desired filtering property by using flat pieces of aluminum and copper, and sometimes casing window 404 is also referred to herein as casing filter 404. In another embodiment, at least some partial heel effect compensation is accomplished by forming casing filter 404 in a wedge shape.

Figure 7:
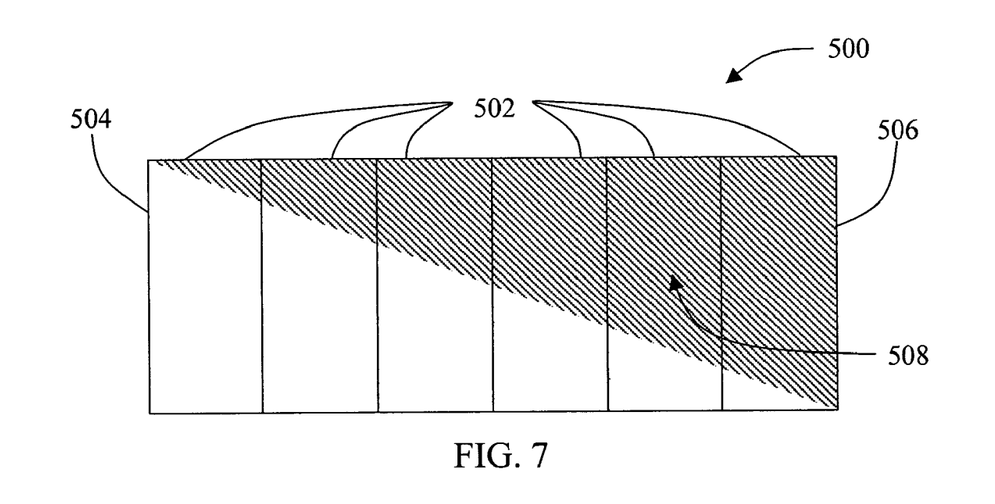
FIG. 7 shows a rectangular, effectively wedge shaped, filter.

FIG. 7 shows a rectangular filter 500, where a plurality of columns 502 are grouped side by side, each column 502 from the left or anode side 504 to the right or cathode side 506 containing a greater consistency of an x-ray attenuating material 508 than the column 502 preceding it. This in effect gives a "wedge shaped" attenuation, although filter 500 is rectangular in shape.

Figure 8:
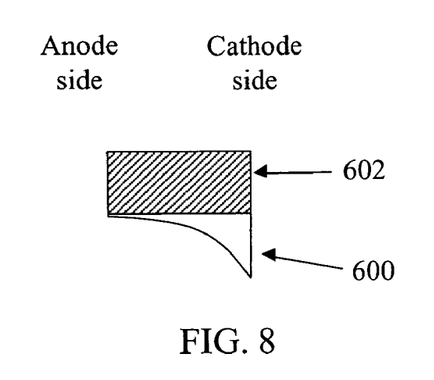
FIG. 8 shows a concave-wedge shaped filter in relation to an x-ray tube window.
Figure 9:
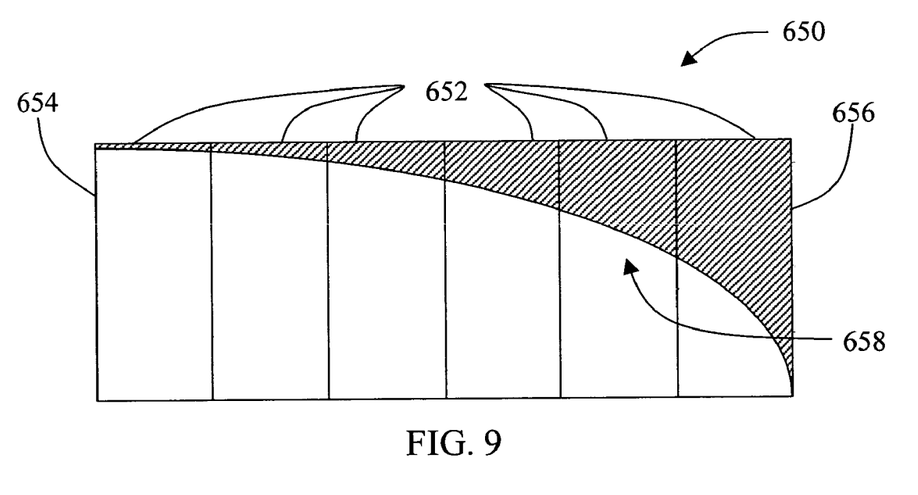
FIG. 9 shows a rectangular, effectively concave-wedge shaped, filter.

FIGS. 8 and 9 illustrate using a concave-wedge shaped filter to provide at least partial target angle heel effect compensation. As used herein, the term "concave-wedge shaped" is defined as a shape including a horizontal top, a concave bottom, a first vertical side and a second vertical side, wherein the first vertical side and the second vertical side are unequal in length.

FIG. 8 shows a concave-wedge shaped filter 600 deposited directly on a x-ray tube casing window 602. FIG. 9 illustrates a rectangular filter 650 where a plurality of columns 652 are grouped side by side, each column 652 from the left or anode side 654 to the right or cathode side 656 containing a greater consistency of an x-ray attenuating material 658 than the column 652 preceding it. This in effect gives a "concave-wedge shaped" attenuation, although filter 650 is rectangular in shape.

Exemplary embodiments of a wedge shaped heel effect compensation filter are described above in detail. The assemblies are not limited to the specific embodiments described herein, but rather, components of each assembly may be utilized independently and separately from other components described herein.

While the invention has been described in terms of various specific embodiments, those skilled in the art will recognize that the invention can be practiced with modification within the spirit and scope of the claims.

What is claimed is:

1. A method of at least partially compensating for an X-ray tube target angle heel effect, said method comprising:
positioning a filter having an anode side and a cathode side between an X-ray source and an X-ray detector, wherein the cathode side has a higher attenuation coefficient than the anode side, and wherein the attenuation coefficient is determined to at least partially compensate for the target angle heel effect.

2. A method in accordance with claim 1 wherein said positioning a filter comprises positioning a wedge shaped filter, wherein the wedge shape comprises a horizontal top, a bottom, a first vertical side and a second vertical side, wherein the horizontal top and the bottom are not parallel and wherein the first vertical side and the second vertical side are unequal in length.

3. A method in accordance with claim 2 wherein said positioning a wedge shaped filter comprises depositing a material on an X-ray tube window to form a wedge shaped filter.

4. A method in accordance with claim 3 wherein said depositing a material comprises depositing aluminum on an X-ray tube window to form a wedge shaped filter.

5. A method in accordance with claim 3 wherein said depositing a material comprises depositing copper on an X-ray tube window to form a wedge shaped filter.

6. A method in accordance with claim 2 wherein said positioning a wedge shaped filter comprises positioning the wedge shaped filter proximate an X-ray tube casing filter separated from an X-ray tube window by an oil gap.

7. A method in accordance with claim 6 wherein said positioning a wedge shaped filter further comprises positioning an aluminum wedge shaped filter.

8. A method in accordance with claim 6 wherein said positioning a wedge shaped filter further comprises positioning a copper wedge shaped filter.

9. A method in accordance with claim 2 wherein the second vertical side comprises a length between 0.5 mm and 1.5 mm thicker than the first vertical side.

10. A method in accordance with claim 9 wherein the second vertical side comprises a length of 1 mm greater than the first vertical side.

11. A method in accordance with claim 1 wherein said positioning a filter comprises positioning a concave-wedge shaped filter, wherein the concave-wedge shape comprises a horizontal top, a concave bottom, a first vertical side and a second vertical side, wherein the first vertical side and the second vertical side are unequal in length.

12. An X-ray tube comprising:
   an anode;
   a cathode;
   a beryllium window; and
   a material deposited on said window, wherein said material is wedge shaped, wherein said wedge shape comprises a horizontal top, a bottom, a first vertical side and a second vertical side, wherein said horizontal top and said bottom are not parallel and wherein said first vertical side and said second vertical side are unequal in length.

13. An X-ray tube in accordance with claim 12 wherein said material deposited on said window forms a wedge shaped filter on said X-ray tube window.

14. An X-ray tube in accordance with claim 13 wherein said material deposited on an X-ray tube window is aluminum.

15. An X-ray tube in accordance with claim 13 wherein said material deposited on an X-ray tube window is copper.

16. An imaging system for scanning an object comprising:
   a radiation source;
   a radiation detector positioned to receive radiation from said radiation source;
   a computer operationally coupled to said radiation source and said radiation detector; and
   a filter having an anode side and a cathode side, positioned between said source and said detector, wherein said cathode side has a higher attenuation coefficient than said anode side, and wherein the attenuation coefficient is determined to at least partially compensate for a target angle heel effect.

17. A system in accordance with claim 16 wherein said filter is wedge shaped, wherein said wedge shape comprises a horizontal top, a bottom, a first vertical side and a second vertical side, wherein said horizontal top and said bottom are not parallel and wherein said first vertical side and said second vertical side are unequal in length.

18. A system in accordance with claim 17 wherein said wedge shaped filter being positioned includes depositing a material on an X-ray tube window to form said wedge shaped filter.

19. A system in accordance with claim 18 wherein said material deposited on an X-ray tube window comprises aluminum.

20. A system in accordance with claim 18 wherein said material deposited on an X-ray tube window comprises copper.

21. A system in accordance with claim 17 wherein said wedge shaped filter being positioned includes positioning said wedge shaped filter proximate an X-ray tube casing filter separated from an X-ray tube window by an oil gap.

22. A system in accordance with claim 21 wherein said wedge shaped filter being positioned comprises aluminum.

23. A system in accordance with claim 21 wherein said wedge shaped filter being positioned comprises copper.

24. A system in accordance with claim 17 wherein said second vertical side comprises a length between 0.5 mm and 1.5 mm thicker than said first vertical side.

25. A system in accordance with claim 24 wherein said second vertical side comprises a length of 1 mm greater than said first vertical side.

26. A system in accordance with claim 16 wherein said filter is concave-wedge shaped, wherein said concave-wedge shape comprises a horizontal top, a concave bottom, a first vertical side and a second vertical side, wherein said first vertical side and said second vertical side are unequal in length.

27. A Computed Tomography (CT) imaging system for scanning an object comprising:
   an X-ray source;
   an X-ray detector positioned to receive X-rays from said source;
   a computer operationally coupled to said X-ray source and said X-ray detector; and
   a filter having an anode side and a cathode side, positioned between said source and said detector, wherein said cathode side has a higher attenuation coefficient than said anode side, and wherein the attenuation coefficient is determined to at least partially compensate for a target angle heel effect.

28. A system in accordance with claim 27 wherein said filter is wedge shaped, wherein said wedge shape comprises a horizontal top, a bottom, a first vertical side and a second vertical side, wherein said horizontal top and said bottom are not parallel and wherein said first vertical side and said second vertical side are unequal in length.

29. A system in accordance with claim 28 wherein said wedge shaped filter being positioned includes depositing a material on an X-ray tube window to form said wedge shaped filter.

30. A system in accordance with claim 29 wherein said material deposited on an X-ray tube window is aluminum.

31. A system in accordance with claim 29 wherein said material deposited on an X-ray tube window is copper.

32. A system in accordance with claim 28 wherein said wedge shaped filter being positioned includes positioning said wedge shaped filter proximate an X-ray tube casing filter separated from an X-ray tube window by oil gap.

33. A system in accordance with claim 32 wherein said wedge shaped filter being positioned is aluminum.

34. A system in accordance with claim 32 wherein said wedge shaped filter being positioned is copper.

35. A system in accordance with claim 28 wherein said second vertical side comprises a length between 0.5 mm and 1.5 mm thicker than said first vertical side.

36. A system in accordance with claim 28 wherein said second vertical side comprises a length of 1 mm greater than said first vertical side.

37. A system in accordance with claim 27 wherein said filter is concave-wedge shaped, wherein said concave-wedge shape comprises a horizontal top, a concave bottom, a first vertical side and a second vertical side, wherein said first vertical side and said second vertical side are unequal in length.

* * * * *

UNITED STATES PATENT AND TRADEMARK OFFICE
CERTIFICATE OF CORRECTION

PATENT NO. : 6,968,042 B2
APPLICATION NO. : 10/661844
DATED : November 22, 2005
INVENTOR(S) : Toth et al.

It is certified that error appears in the above-identified patent and that said Letters Patent is hereby corrected as shown below:

In Claim 32, column 8, line 40, between "by" and "oil" insert --an--.

Signed and Sealed this

Twenty-seventh Day of November, 2007

JON W. DUDAS
*Director of the United States Patent and Trademark Office*